United States Patent [19]

Sherman

[11] Patent Number: 4,877,791

[45] Date of Patent: Oct. 31, 1989

[54] METHOD OF TREATMENT FOR INTERESTITIAL CYSTITIS

[75] Inventor: Fred P. Sherman, Hollywood, Fla.

[73] Assignee: Baker Cummins Pharmaceuticals, Inc., Miami, Fla.

[21] Appl. No.: 265,575

[22] Filed: Nov. 1, 1988

[51] Int. Cl.4 .......................................... A61K 31/485
[52] U.S. Cl. ................................................... 514/282
[58] Field of Search ........................................ 514/282

[56] References Cited

PUBLICATIONS

Goldstein et al., *Ann. Int. Med.*, 98:30–34 (1983).
Simmons et al., *Am. Surg.*, 24:664–667 (1958).
Smith et al., *Arch. Path.*, 93:76–81 (1972).
Parivar et al., *Brit. J. Urol.*, 58:239–244 (1986).
Tomson et al., *Lancet*, Nov. 2, 1985, 1010–1011.
Parsons, *Urology*, 29 (supplement):14–16 (1987).
Feltis et al., *J. Urol.*, 138: 42–43 (1987).
Casale et al., *J. Aller, Clin. Immunol.*, 73:775–781 (1984).

*Primary Examiner*—Shep K. Rose
*Attorney, Agent, or Firm*—Kirschstein, Ottinger, Israel & Schiffmiller

[57] ABSTRACT

A method of treating patients suffering from interstitial cystitis comprises daily administration to such patients of from about 1 to about 50 mg of the narcotic antagonists nalmefene or naltrexone. The nalmefene or naltrexone may be administered in equally divided doses from one to four times daily, preferably by the oral route. Parenteral administration may be utilized where suitable.

8 Claims, No Drawings

METHOD OF TREATMENT FOR INTERSTITIAL CYSTITIS

BACKGROUND OF THE INVENTION

1. Field of the Invention

The invention relates to methods of treating interstitial cystitis.

2. Description of the Prior Art

Interstitial cystitis is a chronic disease of the bladder which affects principally females between 30 and 70 years of age and involves a multitude of urinary and psychiatric complaints such as suprapubic pain on bladder filling, urinary frequency, urinary urgency, dysuria, a sensation of incomplete voiding, malaise, depression and anxiety, among others. The disease is sometimes characterized as "an irritable bladder in an irritable patient."

Histopathalogic examination of bladder biopsy specimens in patients with suspected interstitial cystitis is often used to rule out other diseases (e.g., carcinoma). Typical histopathalogic findings in interstitial cystitis include a non-specific inflammatory reaction, edema and vasodilatation in the submucosa, with or without detrusor fibrosis depending on the stage of the disease. A significant increase in the number of mast cells in the bladder lining, mainly in the detrusor muscle layer, is evident, and the histamine content of the bladder wall is significantly increased. See, e.g., E. M. Meares, *Urology* (Supplement), vol. 29, pp. 46–48 (1987 ); W. L. Lynes et al., *J. Urology*, vol. 138pp. 746-52 (1987); and J. Kastrup et al., *Brit. J. Urology*, vol. 55, pp. 495-500 (1983).

Recent studies indicate that the type of mast cells present in inflammatory bladder conditions such as interstitial cystitis may be of a special type know as mucosal mast cells, which are differentiated morphologically and histochemically from mast cells found, for example, in connective tissue. See J. Cornish et al., *Int. Archs. Allergy Appl. Immun.*, vol. 81 , pp. 337–42 (1986).

The progressive effects of interstitial cystitis on patients are severe and debilitating. Urinary frequency, urgency and pain, among other classic symptoms, impact dramatically and adversely on the patients' quality of life and drive them to seek any possible treatment to alleviate this disorder.

Various drug treatments have been attempted for interstitial cystititis including the oral administration of steroids, antihistamines, anticholinergics, antispasmodices, non-steroidal anti-inflammatory agents, tranquilizers and narcotics. More recently, oral sodium pentosanpolysulfate (Elmiron) has been used in clinical trials to treat interstitial cystitis with mixed results. While some studies reported that a significant number of patients benefited form Elmiron treatment, e.g., A. Fritjoffson et al., *J. Urology*, vol. 138, pp. 507-12 (1987) and C. L. Parsons et al., *J. Uroloqy*, vol. 138, pp. 513-16 (1987), at least one double-blind, controlled trial found no statistically or clinically significant effect of Elmiron in comparison with placebo, M. Holm-Bentzen et al., *J. Uroloqy*, vol. 138, pp. 503-07 (1987). A significant drawback of oral Elmiron therapy for interstitial cystitis is the fact that the drug is primarily liver-metabolized and excreted only to the extent of about 4% in the urine. This means that only a small portion of the drug ingested actually reaches the disease site in the bladder. Furthermore, Elmiron has a relatively short duration of action and must be taken three or four times daily to achieve even the level of symptomatic relief shown in some studies.

Dimethyl sulfoxide (DMSO) has been utilized to a significant degree in the treatment of interstitial cystitis, primarily through intravesical injection of a 50% solution. The DMSO is usually administered initially every two weeks for a total of four to six treatments. After this initial course, intermittent treatments are given if and when symptoms recur.

There are a number of undesirable aspects of intravesical DMSO treatment. The procedure involves substantial discomfort and inconvenience for the patient, requiring the anesthetization of the urethra, insertion of a urethral catheter, emptying of the bladder and instilling of the DMSO into the bladder before removing the catheter. In addition, some patients experience a pronounced sensation of urethral burning during voiding after DMSO treatment and most patients experience a garlic-like odor to their breath and a similar taste in their mouths for 24 hours or more. A smaller number of patients complain of bladder spasms and irritability after DMSO treatments. See G. R. Sant, *Urology* (Supplement), vol. 29, pp. 17–21 (1987). According to Sant, intravesical DMSO results in satisfactory symptomatic improvement in only about 66 to 71% of patients, and in most patients no significant improvement in bladder capacity or endoscopic appearance of the bladder is reported.

Other modalities of treatment for interstitial cystitis have been utilized, including subcutaneous and intravesical injection of heparin, intravesical injection of silver nitrate and bladder distension. To the present date, no method of treatment or pharmaceutical agent for interstitial cystitis has been developed which provides safe and effective symptomatic relief with few adverse side effects and little patient discomfort. Indeed, none of the treatment modalities currently employed even provide symptomatic relief to patients on a consistent basis, apart from the expense, discomfort and inconvenience which they entail.

SUMMARY OF THE INVENTION

It is the object of the present invention to provide a method of treatment for interstitial cystitis which avoids the aforementioned drawbacks of the prior art treatment methods while achieving dramatic symptomatic relief even in cases which have not responded to other treatments. In keeping with this object and others that will become apparent hereinafter, the present invention resides in the daily administration to patients suffering from interstitial cystitis of from about 1 to about 50 milligrams of either of the narcotic antagonists nalmefene or naltrexone, preferably by the oral route. Nalmefene has been found to provide excellent symptomatic relief for interstitial cystitis even where all known treatment modalities have failed.

DETAILED DESCRIPTION OF THE INVENTION

Nalmefene (6-methylene-6-desoxy-N-cyclopropylmethyl-14-hydroxydihydronormorphine) is a long-acting, orally available, potent narcotic antagonist with pure antagonist activity. Apart from its utility in antagonizing the sedation, respiratory depression and other actions of opioid agents, nalmefene has also been found useful in treating diverse conditions such as hyperkinesia in children (U.S. Pat. No. 4,454,142), senile dementia, (U.S. Pat. No. 4,511,570) and sudden infant death syndrome (U.S. Pat. No. 4,639,455), among others. Nalmefene has not hitherto been disclosed, however, as having any utility in the treatment of interstitial cystitis or any related conditions.

Naltrexone (N-cyclopropylmethyl-14-hydroxydihydromorphinone) is another orally available narcotic antagonist with pure antagonist activity. Naltrexone has additionally been disclosed as useful for inducing anorexia (U.S. Pat. Nos. 4,477,457; 4,478,840) and for treating shock (U.S. Pat Nos. 4,267,182; 4,434,168) but not for the treatment of interstitial cystitis or any related condition.

The method of the present invention consists of the daily administration to patients suffering from interstitial cystitis of from about 1 to about 50 mg of nalmefene or naltrexone. The oral route of administration is preferred so that the patient can self-medicate. Nalmefene and naltrexone, unlike certain other narcotic antagonists (e.g. naloxone), are highly effective and substantially bioavailable when administered orally. Nalmefene and naltrexone can be administered parenterally as well, however, for purposes of the present invention.

In accordance with the present invention, nalmefene or naltrexone may be administered to patients suffering from interstitial cystitis in any conventional oral or parenteral dosage form. Oral dosage forms may include tablets, capsules, caplets, liquids, and the like, including generally from about 0.5 to about 25.0 mg of nalmefene or naltrexone per dosage unit together with suitable pharmaceutically acceptable excipients, binders, sweeteners, coloring agents and other conventional additives. Parenteral dosage forms may include any conventional injectable solutions of nalmefene, for example an isotonic saline solution together with pharmaceutically acceptable preservatives and buffers. The parenteral dosage forms generally contain from about 0.5 to about 25.0 mg of nalmefene or naltrexone and may be injected by the subcutaneous, intramuscular, intravenous or intravesical routes.

By one preferred method, the nalmefene or naltrexone may be initially administered to patients in two daily doses of 1 or 2 mg each, with gradual increments of 1 or 2 mg b.i.d. up to a maximum of 25 mg b.i.d.

The method of the present invention provides dramatic symptomatic relief for patients suffering from interstitial cystitis even where conventional modalities of treatment have failed. Patients receiving nalmefene or naltrexone treatment will experience a decrease in urinary frequency and suprapubic pressure, and are able to carry on their daily activities in a relatively normal fashion in comparison with their pre-treatment state.

It is theorized that the mechanism by which nalmefene and naltrexone are able to relieve the symptoms of interstitial cystitis may involve the suppression of histamine release by the mucosal mast cells that have been found to proliferate in the bladder wall of patients suffering from the disease. Although conventional antihistamines have not been found effective in treating interstitial cystitis, that may be attributable to the fact that these drugs are primarily effective in suppressing degranulation of mast cells different from those found in the bladder mucosa, and may have little effect on the mucosal mast cells implicated in interstitial cystitis.

Nalmefene is particularly well-suited for the treatment of interstitial cystitis because of its long duration of action. Unlike Elmiron, nalmefene need only be administered from one to two times daily to achieve symptomatic relief, although equally divided doses administered from one to four times daily may be utilized. In addition, while Elmiron is excreted only to a small degree through the bladder, nalmefene is excreted in the urine as the glucuronide (as is naltrexone). Unlike intravesical DMSO treatments, nalmefene and naltrexone may be taken by patients in the oral form at their convenience with no accompanying discomfort and relatively little expense. Moreover, there are few reports of any significant adverse effects with nalmefene or naltrexone therapy at the dosage levels proposed by the present invention, unlike many of the pharmaceutical agents conventionally used to treat interstitial cystitis.

The following example provides a detailed illustration of the method of the present invention. This example is not intended to limit or restrict the scope of the invention in any way, and should not be construed as providing dosage forms, regimens or methods of administration which must be utilized exclusively to practice the invention.

EXAMPLE

A 64 year old female patient exhibiting the classic symptoms of interstitial cystitis had undergone a variety of treatment modalities, all of which failed to provide symptomatic relief. The diagnosis of interstitial cystitis was confirmed by bladder biopsy. The patient then received 1.0 mg tablets of nalmefene twice daily for seven days after which the dosage was increased in weekly increments of 1 mg b.i.d. until she was receiving 9 mg b.i.d.

By the third week, the patient noted a significant decrease in urinary frequency and suprapubic pressure, and reported that for the first time in many years she was able to go to work without having to urinate every 15 minutes. The patient continued to report increasing symptomatic relief as the dosage level was increased.

It has thus been shown that there are provided methods which achieve the various objects of the invention and which are well adapted to meet the conditions of practical use.

As various possible embodiments might be made of the above intention, and as various changes might be made in the embodiments set forth above, it is to be understood that all matters herein described are to be interpreted as illustrative and not in a limiting sense.

What is claimed as new and desired to be protected by Letters Patent is set forth in the following claims.

1. A method of treating a patient suffering from interstitial cystitis comprising the daily administration to the patient of from about 1 to about 50 mg of nalmefene or naltrexone.

2. A method according to claim 1 wherein the nalmefene or naltrexone is administered to the patient orally.

3. A method according to claim 2 wherein the nalmefene or naltrexone is administered to the patient in an oral dosage form comprising a tablet, capsule, caplet or liquid containing from about 0.5 to about 25.0 mg of nalmefene.

4. A method according to claim 1 wherein the nalmefene or naltrexone is administered to the patient parenterally.

5. A method according to claim 4 wherein the nalmefene or naltrexone is administered to the patient by the subcutaneous, intramuscular, intravenous or intravesical routes.

6. A method according to claim 1 wherein the nalmefene or naltrexone is administered to the patient from one to four times daily.

7. A method according to claim 6 wherein the nalmefene or naltrexone is administered to the patient from one to two times daily.

8. A method according to claim 7 wherein 1 mg of nalmefene or naltrexone is administered to a patient twice daily for an initial period, after which the dosage amount is gradually increased to a maximum of 25 mg twice daily.

* * * * *